United States Patent [19]

Lacks

[11] Patent Number: 4,960,707
[45] Date of Patent: Oct. 2, 1990

[54] RECOMBINANT PLASMIDS FOR ENCODING RESTRICTION ENZYMES DPNI AND DPNII OF STREPTOCOCCUS PNEUMONTAE

[75] Inventor: Sanford A. Lacks, Brookhaven, N.Y.

[73] Assignee: Associated Universities, Inc., Washington, D.C.

[21] Appl. No.: 85,944

[22] Filed: Aug. 17, 1987

[51] Int. Cl.[5] .................. C12N 15/00; C12N 9/16; C12N 1/20
[52] U.S. Cl. .................. 435/320; 435/172.3; 435/196; 435/252.3; 935/14; 935/29
[58] Field of Search .................. 435/172.3, 252.3, 196, 435/320; 935/14

[56] References Cited

U.S. PATENT DOCUMENTS

| | | | |
|---|---|---|---|
| 4,371,625 | 2/1983 | Tiollais | 435/317 |
| 4,374,927 | 2/1983 | Sninsky | 435/68 |
| 4,436,815 | 3/1984 | Hershberger et al. | 435/172 |
| 4,460,688 | 7/1984 | Sanders | 435/172.3 |
| 4,506,013 | 3/1985 | Hershberger | 435/172.3 |
| 4,579,821 | 4/1986 | Palmiter | 435/172.3 |
| 4,650,761 | 3/1987 | Hershberger et al. | 435/172.3 |
| 4,729,954 | 3/1988 | Lacks | 435/172.3 |

OTHER PUBLICATIONS

Lacks et al., *Cell* 46:993–1000 (1986).
Lacks et al., In *Streptococcal Genetics*, (Ferretti and Curtiss, eds.), American Society for Microbiology, Washington, D.C., pp. 31–41 (1987).
Lacks et al., *J. Bacteriol.*, 158:905–909 (1984).
Lacks et al., *J. Bacteriol.*, 157:934–936 (1984).
Stassi, et al., Proc. Natl. Acad. Sci., USA, vol. 78, No. 11, pp. 7028–7032 (Nov. 1981).
Muckerman, et al., J. Bact., vol. 152, No. 1, pp. 183–190 (Oct. 1982).
Lopez, et al., Mol. Gen. Genet., vol. 195, pp. 402–410 (1984).
Mejean, et al., J. Bact., vol. 158, No. 3, pp. 1175–1178 (Jun. 1984).
Balganesh, et al., Gene, vol. 29, pp. 221–230 (1984).
Minkley, et al., J. Biol. Chem., vol. 259, No. 16, pp. 10386–10392 (Aug. 1984).
Mannarelli, et al., Proc. Natl. Acad. Sci. USA, vol. 82, pp. 4468–4472 (Jul. 1985).
Lacks, et al., Cell, vol. 46, pp. 993–1000, (Sep. 1986).
Lacks, et al., Strep, Genet., Published by Am. Soc. for Microbiology, pp. 31–41 (Jun. 1987).

Primary Examiner—Thomas Mays
Attorney, Agent, or Firm—Margaret C. Bogosian

[57] ABSTRACT

Chromosomal DNA cassettes containing genes encoding either the DpnI or DpnII restriction endonucleases from *Streptococcus pneumoniae* are cloned into a streptococcal vector, pLS101. Large amounts of the restriction enzymes are produced by cells containing the multicopy plasmids, pLS202 and pLS207, and their derivatives pLS201, pLS211, pLS217, pLS251 and pLS252.

6 Claims, 9 Drawing Sheets

RECOMBINANT PLASMIDS FOR ENCODING RESTRICTION ENZYMES DPNI AND DPNII OF STREPTOCOCCUS PNEUMONTAE

The U.S. Government has rights in this invention pursuant to Contract Number DE-AC02-76CH00016, between the U.S. Department of Energy and Associated Universities Inc.

UTILITY STATEMENT

Cells of *Streptococcus pneumoniae* contain either DpnI, a restriction endonuclease that cleaves only the methylated DNA sequence 5'-GmeATC-3', or DpnII, a restriction enzyme which cleaves the same sequence when it is not methylated. Chromosomal DNA cassettes containing genes encoding either the DpnI or DpnII restriction systems were cloned in the streptococcal vector, pLS101. Large amounts of the restriction enzymes DpnI and DpnII were produced in cells containing the multicopy plasmids pLS202 and pLS207. Cloning of the restriction enzymes DpnI and DpnII permits their production in large amounts. These enzymes in purified form are then available for transfer to other organisms, which would thereby be given the ability to make the enzymes.

Cells containing these recombinant plasmids provide a convenient source for these restriction enzymes; these enzymes can be used in studies of DNA and restriction enzyme structure, and in the differentiation of methylated and unmethylated DNA. It is also anticipated that these enzymes will be useful in the prevention of infection of cultures by bacterial viruses; thus the cloned streptococcal restriction genes should be useful in the dairy industry for preventing viral attack on cultures.

STATEMENT OF DEPOSIT

The plasmids of the present invention have been deposited in the American Type Culture Collection, in Rockville, Md., under conditions which assure maintenance of the deposits in accordance with the rules established under M.P.E.P. 608.01(p). Plasmid pLS101 may be obtained under ATCC No. 39938; pLS202 under ATCC No. 67490; pLS207 under ATCC No. 67491; pLS211 under ATCC No. 67493; pLS252 under ATCC No. 67494; and pLS21 under ATCC No. 67492.

BACKGROUND OF THE INVENTION

Figure 1A:
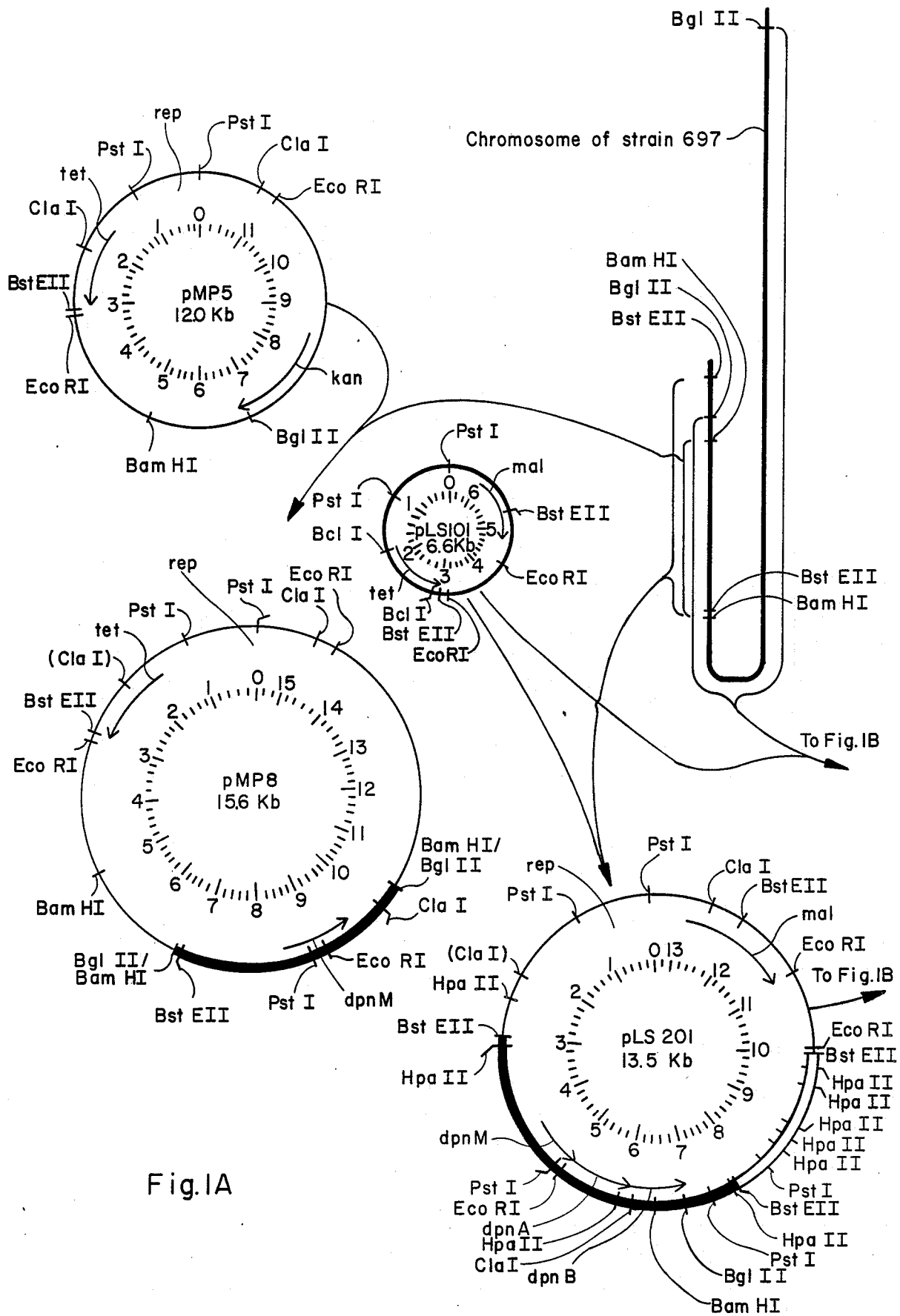
FIGS. 1A and 1B. Cloning of the DpnII restriction genes. Solid bar, chromosomal DNA from the DpnII region; open bar, adventitious chromosomal DNA; thin line, vector. Arrows between plasmids indicate derivation. The region essential for replication of the plasmids, rep, and the extent and direction of transcription of intact plasmid-borne genes are indicated.

The restriction endonucleases DpnI and DpnII were first found in derivatives of common laboratory strains of *Streptococcus penumoniae*. The former enzyme is unique among restriction endonucleases because it cleaves only the methylated DNA sequence 5'-GmeATC-3'; while DpnII cleaves only the non-methylated form of the same DNA sequence. Restriction endonucleases generally act on specific sequences in DNA and are blocked in their action by methylation of the sequences. DpnI, the unusual restriction endonuclease found in *Streptococcus pneumoniae*, is produced in large quantities by the plasmids pLS207, pLS217, pLS218, pLS251 and pLS252 of the present invention. No modification of the DNA in cells that produce DpnI is necessary to protect it from the enzyme. However, not all strains of *S. penumoniae* contain DpnI; others contain the complementary enzyme DpnII, which attacks the unmethylated sequence 5'-GATC-3'. As with ordinary restriction systems, cells that produce DpnII also produce a DNA methylase that modifies the site, making it susceptible to DpnI. Restriction endonuclease DpnII is produced in large quantities by plasmid pLS201, pLS202 and pLS211 of the present invention.

DNA sequencing and hybridization results show that the DpnI and DpnII gene segments are unrelated. Furthermore, the hybridization results show that the genes responsible for one restriction phenotype are not present in cells of the opposite phenotype.

The determination of restriction phenotype appears to be based on a mechanism of intercellular exchange of genetic cassettes. Cassettes are defined for the purpose of the present invention as compact structures containing alternate forms of information that can be inserted into a common location from which their information can be expressed. The presence of homologous DNA proximal and distal to both restriction gene cassettes shows both sets of restriction genes to be located in the same position in the chromosome of *S. pneumoniae*.

Transformation-mediated recombination, a natural process in this species, makes use of the adjacent homology to transfer restriction cassettes from one strain to another. Replacement of a functional DpnI cassette by a DpnII cassette has been accomplished by the use of a null intermediate [Muckerman, et al., *J. Bacteriol.*, 152: 183-190 (1982)].

Restriction enzymes or endonucleases are site-specific endodeoxyribonuclease enzymes which cause cleavage of both strands of DNA. These enzymes are common among bacteria, where they function to prevent infection by bacterial viruses. DpnI and DpnII restrict viruses produced in cells of the opposite phenotype to an infection frequency of $<10^{-5}$. In contrast, transforming DNA is not affected, indicating that the restriction enzymes are not designed to exclude foreign DNA in general. It is believed that the purpose of these complementary restriction systems in *S. pneumoniae* is the protection of the species from viral destruction. The presence of complementary restriction systems in different cells among natural populations ensures the survival of at least some of the population after an epidemic infection initiated in a cell of one particular restriction phenotype.

In a viral epidemic of the sort postulated, DNA containing restriction gene cassettes corresponding to the susceptible phenotype are released from killed cells. This DNA could conserve the genetic information encoding that restriction system by passing it on in subsequent transformation. Restriction cassettes in the form of free DNA, either inside (as single strands prior to integration) or outside the bacterial cell, would not be expressed.

Figure 3A:
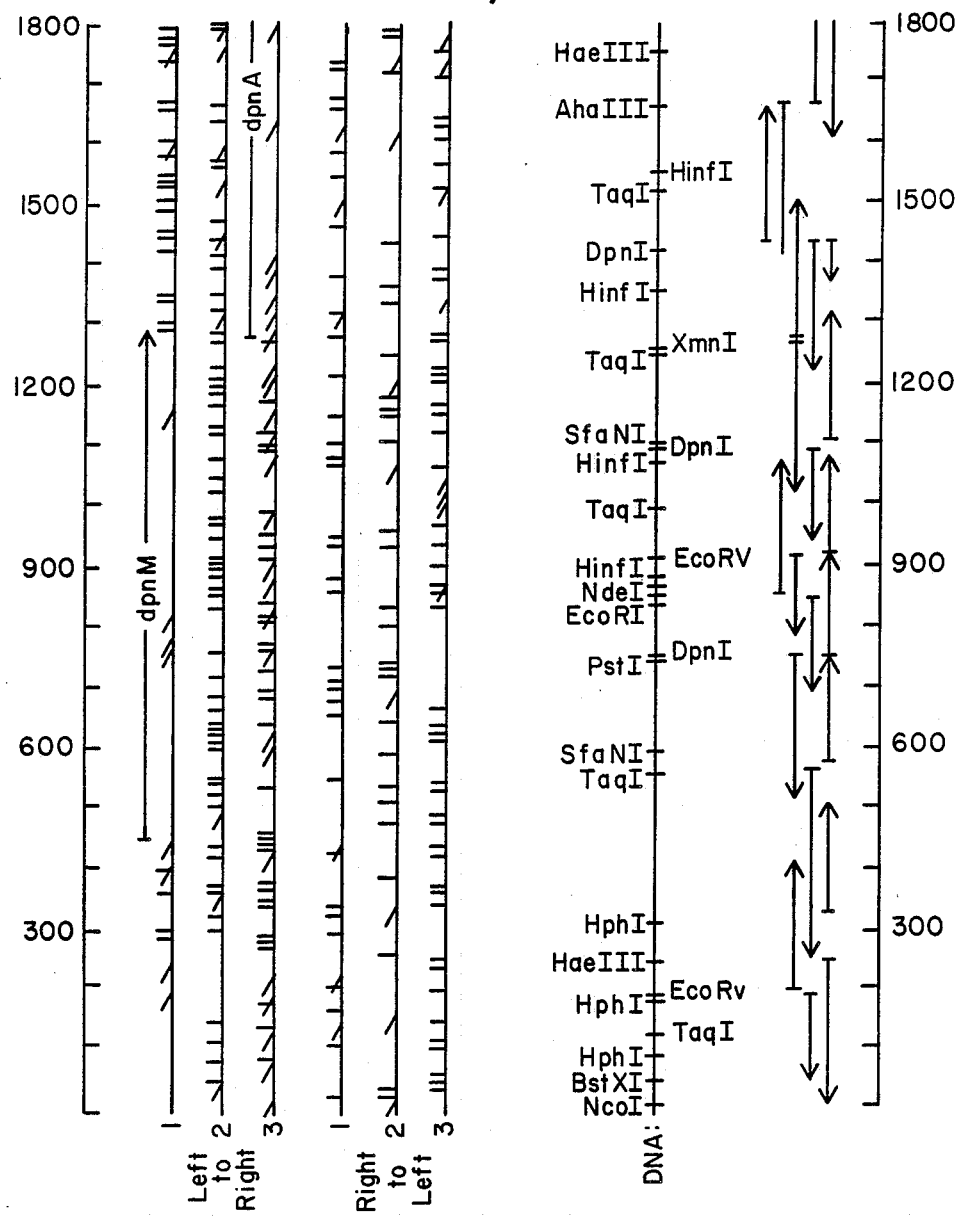
FIGS. 3A and 3B. Restrictuon map of DpnII gene region showing DNA sequencing strategy and open reading frames. Segments for which nucleotide sequence was determined are shown below restriction site map by arrows indicating the strand sequenced: vertical marks, 5'-labeled terminus; arrowhead, end of reading. Open reading frames are indicated above the map for all three phases in both directions: vertical marks, termination codons; oblique marks, potential ATG start sites. DpnII-specific genes are indicated by arrows.
Figure 3B:
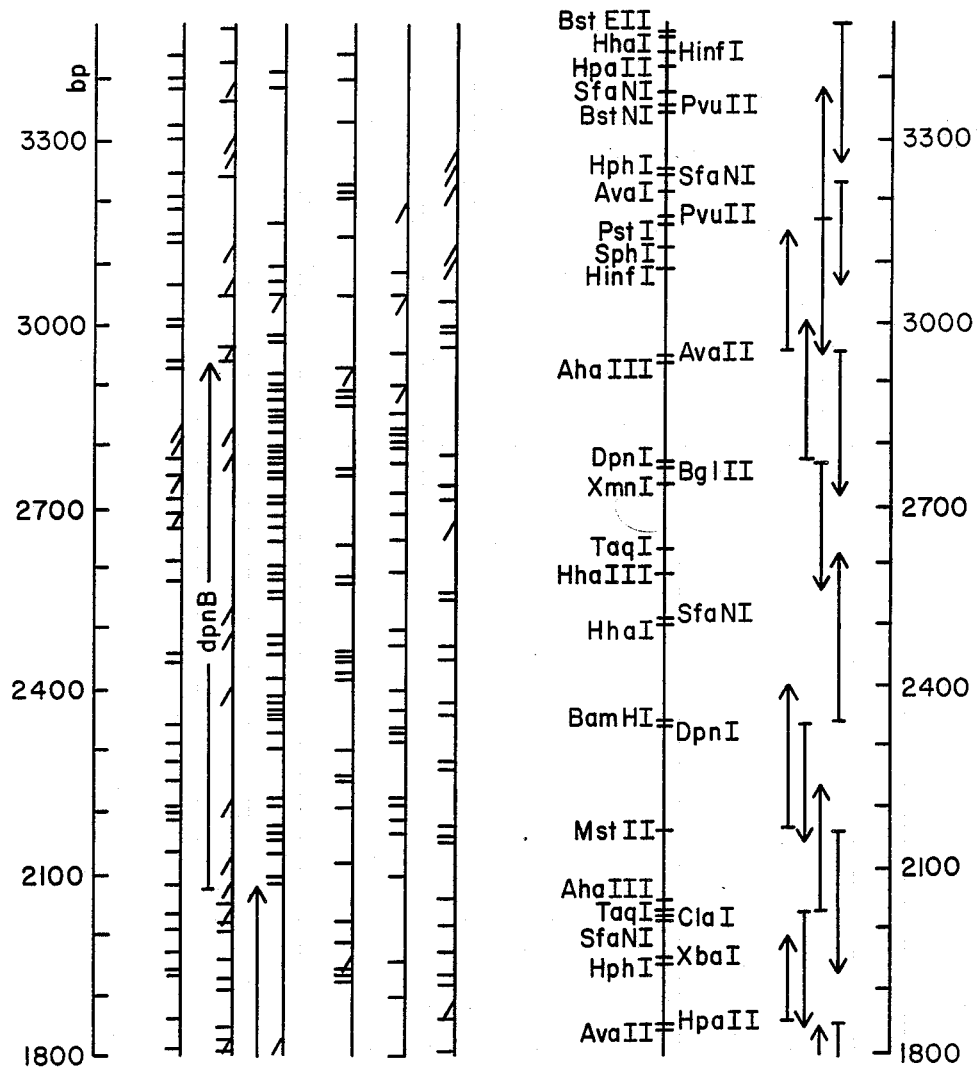

Two of the plasmids of the present invention, plasmids pLS201 and pLS207, produce large quantities of their respective restriction endonucleases. The nucleotide sequence of a 3.5 kb segment of pLS201 (terminating at the distal BstEII site of the chromosomal insert), which contains the DpnII genes, is illustrated in FIG. 3. The segment contains an open reading frame leading into the left end of the segment, followed by three extensive open reading frames completely contained within the segment. Polypeptides encoded by the open reading frames are shown beginning with fMet at putative ATG start codons and terminating at the following step codon. The first complete gene, dpnM, encodes a 33 kd polypeptide identified as the DpnII DNA methylase. A strong ribosome-binding site is associated with an ATG codon near the beginning of the second full reading frame. The 31 kd polypeptide encoded by this gene, called dpnA, also functions, independently, to methylate 5'-GATC-3' sites. The next open reading frame also contains a typical ribosome-binding site. The coding region for this polypeptide overlaps the preceeding one by 11 bases, and encoded the product of the third gene (dpnB), a 34 kd polypeptide corresponding to the DpnII endonuclease.

Figure 4:
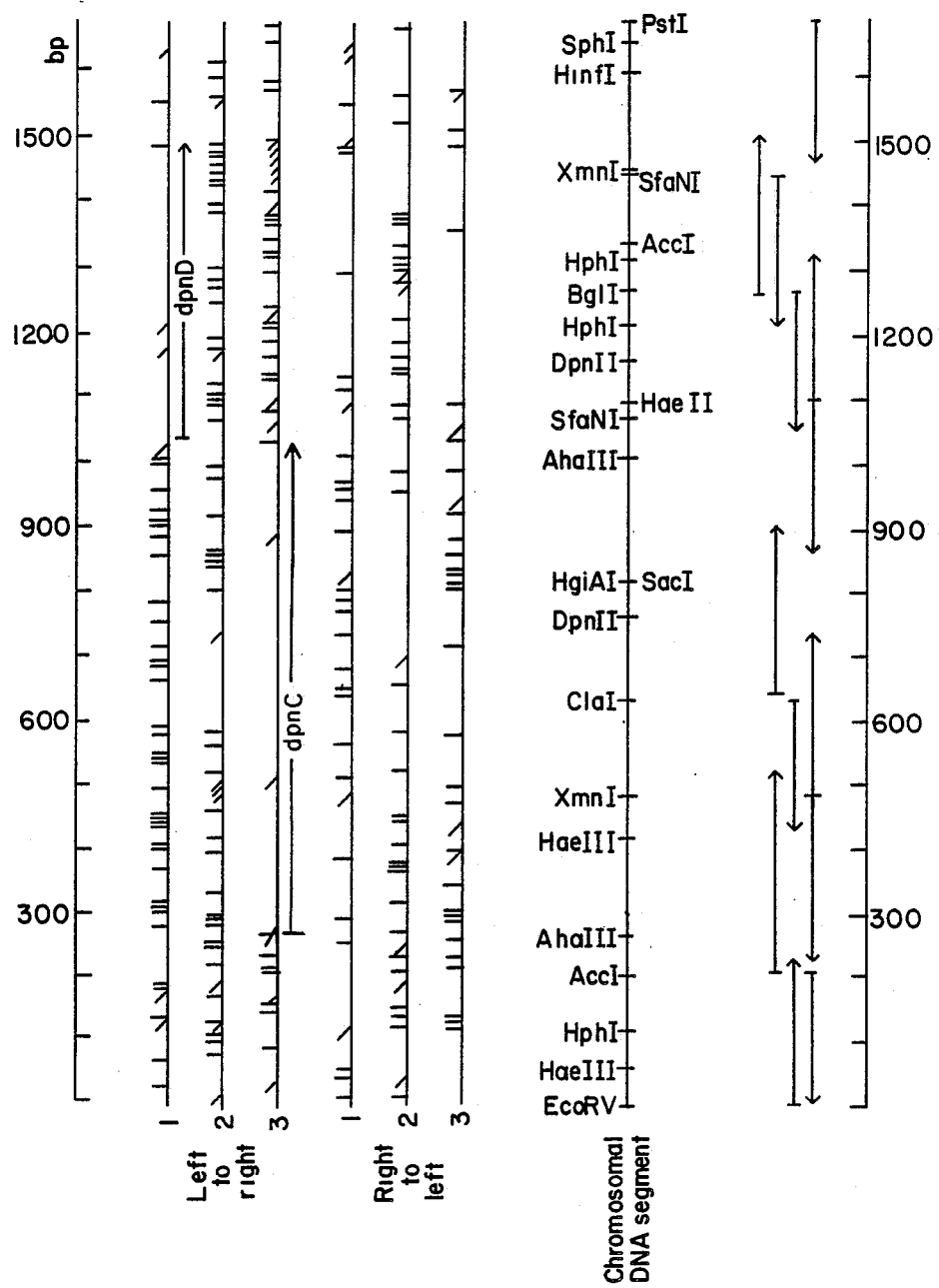
FIG. 4. Restriction map of DpnI gene region showing DNA sequencing strategy and open reading frames. Symbols as in FIG. 3 except arrows indicate DpnI-specific genes.
Figure 5:
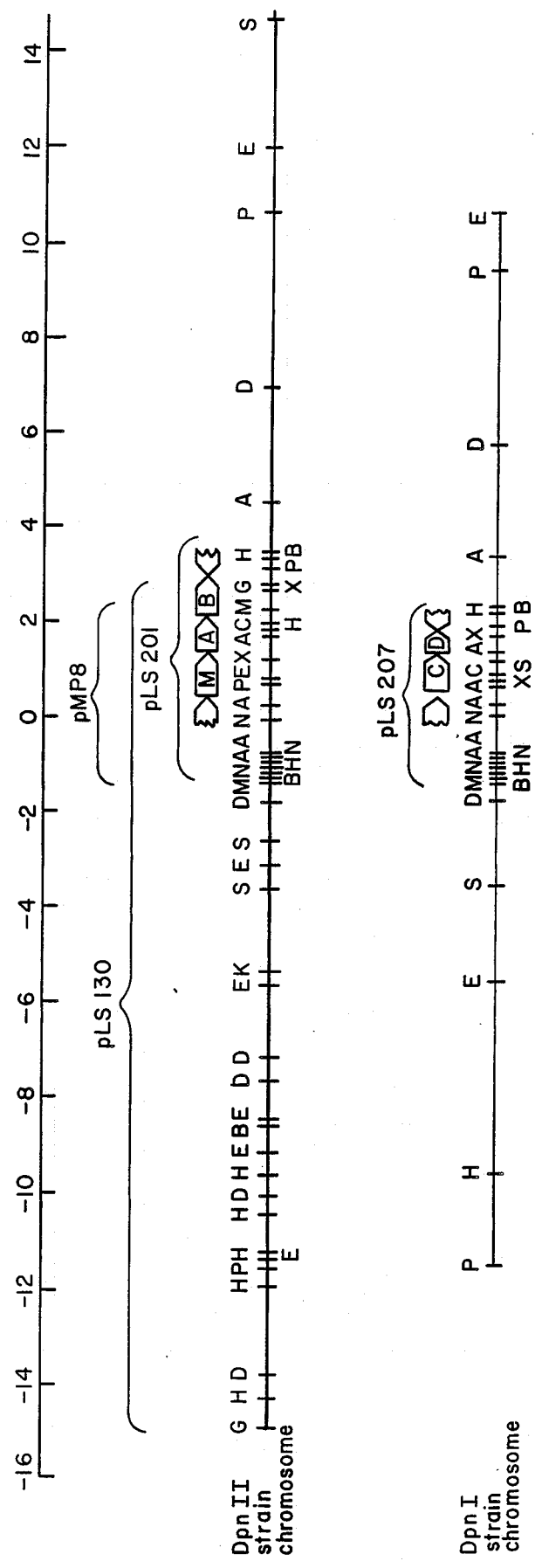
FIG. 5. Restriction gene cassettes revealed by DNA sequencing and hybridization. Open boxes indicate polypeptides encoded by open reading frames; pointed ends show direction of transcription and letters indicate Dpn gene products. Restriction sites were determined by cleavage of plasmid inserts or hybridization with chromosomal fragments. Key: HaeIII; B, BstEIII; C, GlaI; D, HindIII; E. EcoRI; G, BglII; H, HpaII; K, KpnI; M, BamHI; N, NcoI; P, PstI; S, SacI; X, XmnI.

A 1.7 kb segment of pLS207 (terminating at the PstI site near the distal end of the chromosomal insert) contains DpnI-specific genes. FIG. 4 shows that an open reading frame enters the segment from the left. The next open reading frame begins at 277 with a potential ATG start site, and encodes a 30 kd polypeptide corresponding to the DpnI endonuclease.

The sequenced segments of DpnI and DpnII differ markedly in their central portions, but the ends are homologous [Lacks, et al., *Cell*, 46: 993-1000 (1986)]. In a 300 bp sequence distal from the EcoRV site common to both segments, 90% of the first 99 bp are identical. For the protein products of this gene from the two different strains, only 3 amino acid differences (all near the carboxy terminus) are evident. The homology ends at the triplet following the stop codon.

Homology at the right or distal ends of DpnI and DpnII segments is evident over a 168 bp stretch in which only two bp are different. The distal 137 nucleotides encode the carboxyl terminus of a protein translated from right to left—opposite the direction of transcription and translation of the dpn products.

SUMMARY OF THE INVENTION

The present invention entails the cloning of chromosomal DNA cassettes containing genes encoding either the DpnI or DpnII restriction endonucleases from *Streptococcus pneumoniae* into a streptococcal vector, plasmid pLS101. Large amounts of the restriction enzymes are produced by cells containing the multicopy plasmids, pLS202 and pLS207 and their derivatives pLS201, pLS211, pLS217, pLS218, pLS251 and pLS252.

Recombinant plasmids containing chromosomal fragments of the DpnII-producing *S. pneumoniae* strains with an intact methylase gene are obtained by transforming a strain of null phenotype with suitably ligated vector and chromosomal DNA, then treating the mixed plasmid pool from the transformed population with DpnII to destroy all but the methylated plasmids. From the surviving plasmids, a 4.6 kg BstEII fragment was isolated and cloned into plasmid vector pLS101 to give plasmid pLS201, a plasmid capable of inducing the production of DpnII endonuclease.

The production of the DpnI plasmid includes chromosomal facilitation of plasmid establishment (i.e. chromosomally-derived sequences supply some of the DNA sequences in the plasmid)—the DpnII gene segment of pLS202 is replaced with the defective DpnI gene segment from the chromosome of *S. pneumoniae* strain 777, resulting in plasmid pLS203. The defective DpnI segment of pLS203 is then replaced (by chromosomal facilitated transfer) by the active DpnI gene segment from the chromosome of strain 193 to give pLS207, the plasmid of the present invention which contains a functional DpnI gene segment.

Furthermore, the present invention includes the one-step production of DpnI-producing plasmids by inserting pLS202 into DpnI-producing cells, thus giving rise, by chromosomal facilitation, to plasmids identical to pLS207.

DETAILED DESCRIPTION OF THE INVENTION

The preferred strains of *S. pneumoniae* used in this invention are the nonencapsulated strains R6, R36NC (identical to Strain 707), Rx, and 8R1. Each of these strains are well known and described in Muckerman, et al., *J. Bacteriol.*, 152: 183-190 (1982). The other strains used in the formation of the plasmids of the present invention are all derived from the above-noted strains: Strains 193 (malDXMP581) is an R6 derivative; Strain 697 (end-1 str) is an 8R1 derivative; and Strain 777 (malDXMP581 end-1) is an Rx derivative. While the present invention is not limited to these bacterial strains, the production of the plasmids of the present invention used a selection technique focusing on the Mal+ marker—*S. pneumoniae* strains noted above, therefore, contained the malDXMP581 deletion in their chromosome.

The *S. pneumoniae* strains contemplated for use in this invention, therefore, are those strains which have, or may be altered to have, an identifiable and selectable marker. These bacterial cultures were grown in casein-hydrolysate-based medium according to Lacks, *Genetics*, 53: 207-235 (1966), and were transformed according to the procedure described in Balganesh, et al., *Gene*, 29: 221-230 (1984).

Plasmid vector pLS101 is described in Balganesh, et al., *Gene*, 29: 221-230 (1984), and is publicly available through the American Type Culture Collection, Accession No. 39938.

Figure 1B:
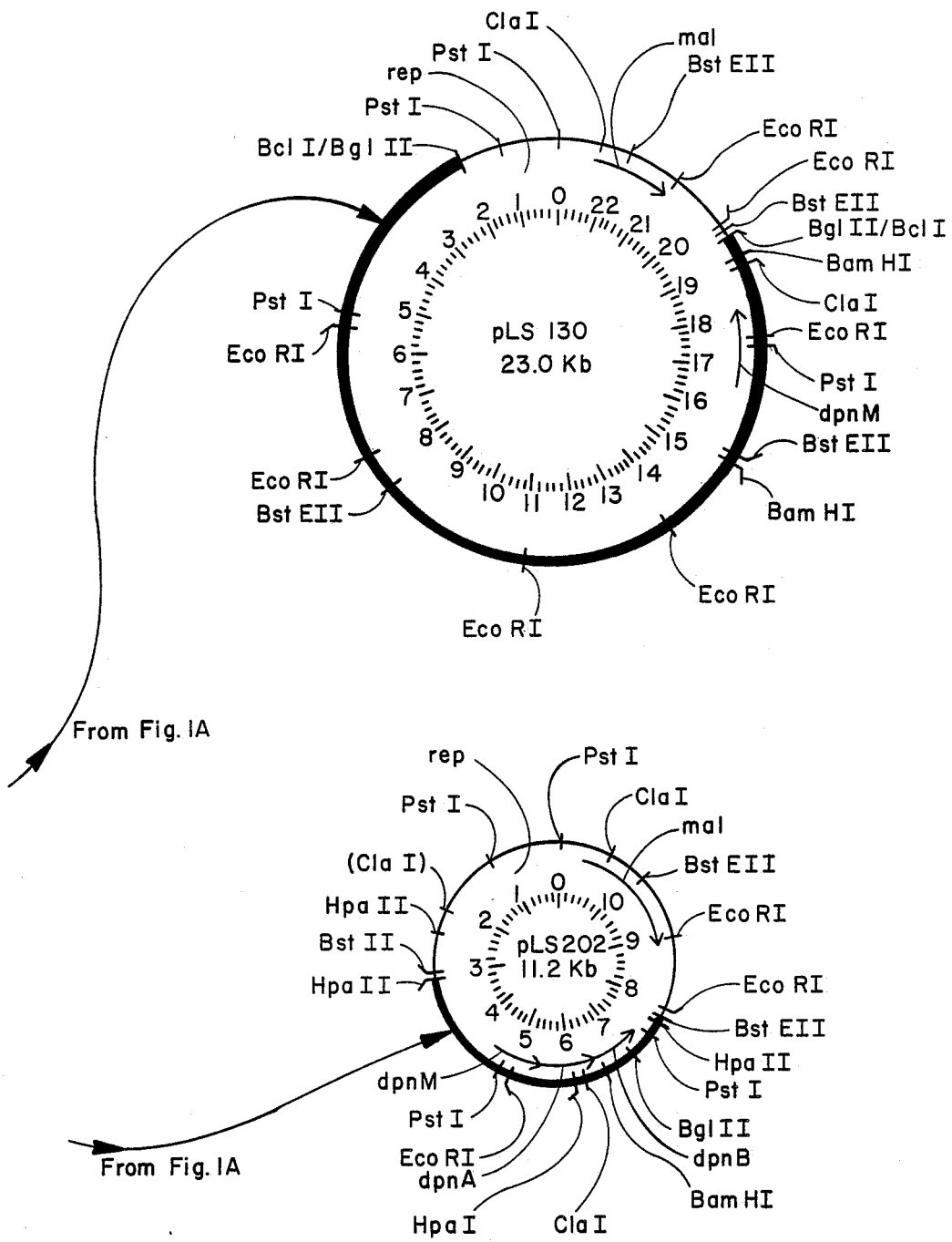
Figure 2:
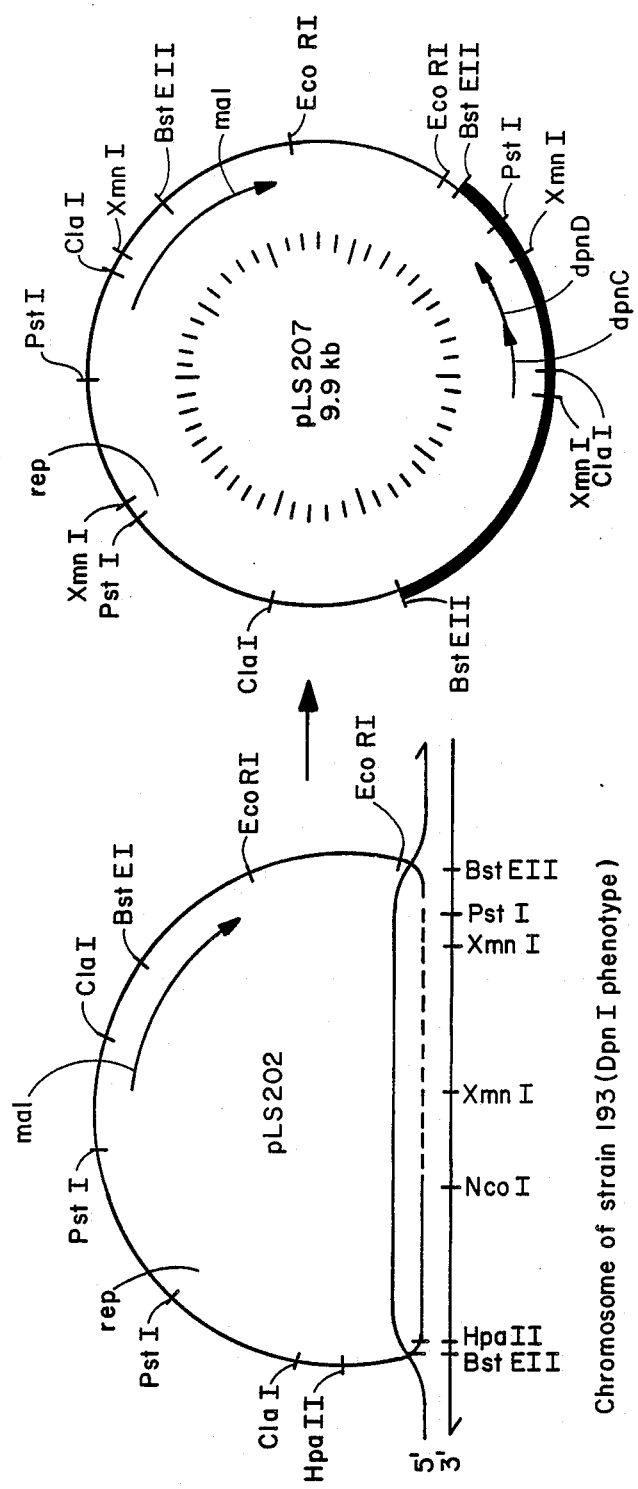
FIG. 2. Cloning of DpnI genes by chromosomal facilitation of plasmid establishment. Replacement during facilitated transfer of pLS202 of its DpnII gene segment by the DpnI gene segment from the chromosome of strain 193 to give pLS207. A single-strand fragment of the donor plasmid interacts by circular synapsis with homologous chromosomal DNA to give a D-loop structure. Dashed line, portion of plasmid strand lost during entry that is resynthesized from the chromosomal template.

The process for cloning the DpnII restriction genes is illustrated in FIG. 1 while the process for cloning the DpnI restriction genes is shown in FIG. 2. DpnII gene sequences are cloned by inserting restriction fragments of chromosomal DNA from *S. pneumoniae* DpnII strain 697 into streptococcal vector plasmid pLS101. That is, a 4.6 kb BstEII fragment from strain 697 is inserted, together with an adventitious chromosomal fragment, into pLS101 linearized with BstEII. This results in plasmid pLS201. The adventitious 2.3 BstEII fragment is then removed to produce one of the plasmids of the present invention, plasmid pLS202, a plasmid which, when placed in a suitable DpnII-producing host, confers the ability to produce DpnII endonuclease.

A different approach is preferred for the production of DpnI-producing plasmids—chromosomal facilitation of plasmid establishment. As illustrated in FIG. 2, the DpnII gene segment of pLS202 is replaced with the DpnI segment from the chromosome of *S. pneumoniae* strain 777. The process occurs due to chromosomal facilitation events in which the pLS202 strand fragment (which lacks the central region of its chromosomal insert) interacts with the recipient chromsome from strain 777. Homologies of sequences which bracket both ends of the DpnI and DpnII gene segments provide the proper environment for plasmid pLS202 to pick up a portion of the null strain 777 chromosomal information in order to produce a new plasmid, pLS203. pLS203, however, contains a defective DpnI segment, which must be replaced by an active segment. Accordingly, replacement during facilitated transfer of the defective DpnI segment of pLS203 by the active DpnI gene segment from the chromosome of *S. pneumonia* strain 193 produces plasmid pLS207, a plasmid which, when placed in a suitable DpnI-producing host, confers the ability to produce DpnI endonuclease.

Alternatively, direct introduction of plasmid pLS202 into DpnI-producing cells gives rise to plasmids identical to pLS207. This mechanism also uses chromosomal facilitation, but requires only a single step.

Chromosomal DNA is prepared from *S. pneumoniae* by the well-known process of Berns, et al., *J. Mol. Biol*, 11: 476-490 (1965). Plasmids are purified according to Currier, et al., *Anal. Biochem.*, 76: 431-441 (1976). Crude plasmid preparations were made by the method of Birnboim, et al., *Nucl. Acids. Res.*, 7: 1513-1523, as modified by Stassi, et al., *PNAS*, 78: 7028-7032 (1981).

Analytical gel electrophoresis of plasmids and restriction fragments is carried out in 1% agarose or 5% polyacrylamide with staining by ethidium bromide. Preparative gel electrophoresis is performed in 0.8% low-melting point agarose, and the DNA is extracted from the gel slices as described in Mannarelli, et al., *PNAS, USA*, 82: 4468-4472 (1985), and ligated according to Stassi, et al. (cited above).

Figure 6:
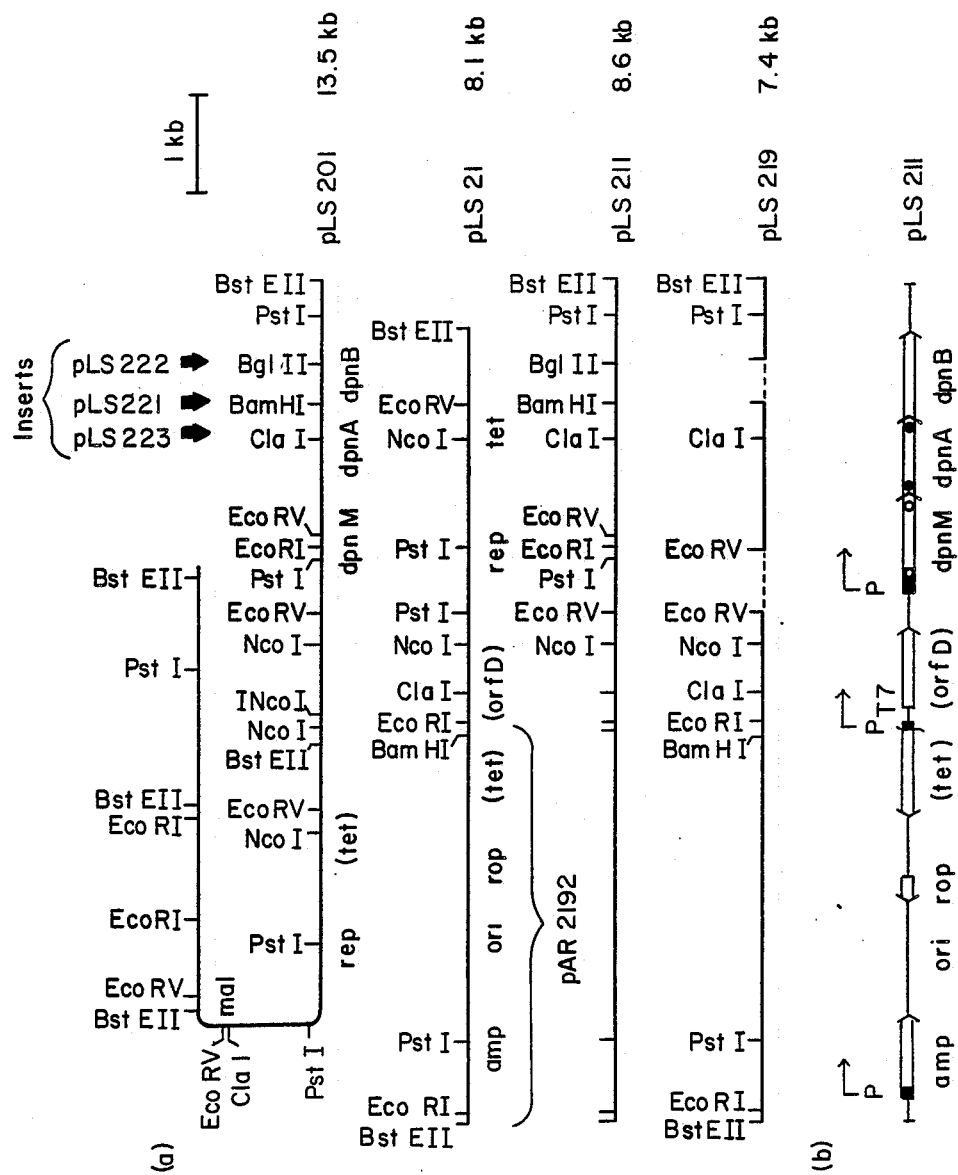
FIG. 6. The construction of plasmid pLS211 from pLS201 and pLS21. All plasmids are shown broken at a BstEII site.
Figure 7:
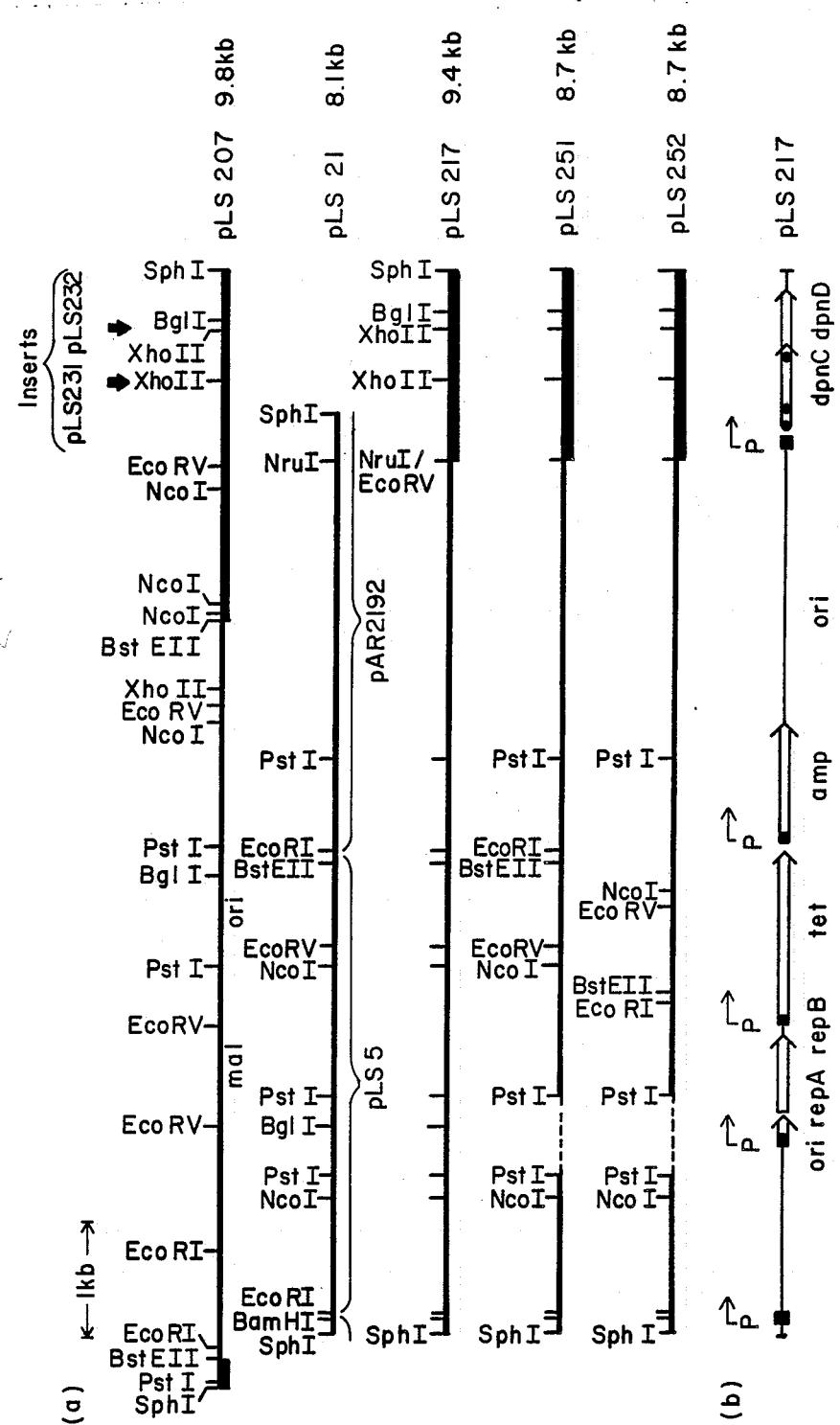
FIG. 7. The construction of plasmids pLS217, pLS251 and pLS252 from pLS207 and pLS21. All plasmids are shown broken at an SphI site. Plasmid pLS218 is identical to pLS217 except for a 1-kb deletion that removed the rightmost PstI site in the pLS5 portion.

Derivative plasmids containing the DpnI and DpnII restriction genes were constructed as follows. The 3.5 kb NcoI-BstEII fragment of pLS201 containing the DpnII genes was ligated to the BstEII-NcoI fragment of pLS21 [Lacks, et al., *J. Mol. Biol.*, 192: 753-765 (1986)] containing the entire pAR2192 portion to give pLS211 on transfer to a strain of *E. coli* (FIG. 6). The advantage of this plasmid, in addition to its transfer to a bacterium that is in wide industrial use, is that it contains a promoter for T7 RNA polymerase, so that when placed in *E. coli* strain BL21(DE3) (Studier and Moffat, *J. Mol. Biol.*, 189: 113-130, 1986), it can produce very large amounts of DpnII gene products. Several derivatives containing DpnI genes that could be propagated in *E. coli*, and that contained the T7 RNA polymerase promoter, were constructed (FIG. 7). A 1.6 kb EcoRI-SphI fragment of pLS207 was ligated to pLS21 cleaved with NruI and SphI to give pLS217, which can replicate in either *S. pneumoniae* or *E. coli*. A spontaneous deletion of pLS217, which removed 1 kb in the vicinity of repB, to pLS218 was more stable in *E. coli* than the parenteral plasmid, but it could not propagate in *S. pneumoniae*. Removal of a 1.0 kb PstI fragment from pLS217 give rise to pLS251 and pLS252, both of which are stable in *E. coli*. Plasmid pLS252 no longer makes β-lactamase, but it still confers tetracycline resistance. Transfer of pLS218, pLS251 or pLS252 to BL21A (DE3)—a dam derivative of BL21(DE3) constructed especially for this purpose—enables production of very large amounts of the DpnI endonuclease.

I claim:

1. Plamid pLS202, deposited in the American Type Culture Collection under ATCC No. 67490, which is characterized as a DpnII cassette and consists essentially of genes dpnM, dpnA and dpnB in a broad-host-range vector.

2. Plasmid pLS207, deposited in the American Type Culture Collection under ATCC No. 67491, which is characterized as a DpnI cassette and consists essentially of genes dpnC and dpnD in a broad-host-range vector.

3. Plasmid pLS211, deposited in the American Type Culture Collection under ATCC No. 67493, which is characterized as a DpnII cassette and consists essentially of genes dpnM, dpnA, and dpnB under control of a phage T7 RNa polymerase promoter in a hyperexpression vector of *E. coli*.

4. Plasmid pLS252, deposited in the American Type Culture Collection under ATCC No. 67494, which is characterized as a DpnI cassette and consists essentially of genes dpnC and dpnD under control of a phage T7 RNA polymerase promoter in a hyperexpression vector of *E. coli*.

5. A recombinant DNA plasmid comprising a bacterial plasmid which contains a functional DpnI gene segment wherein said plasmid results in the production of DpnI enzyme following the transformation thereof into a bacterial strain suitable for production of DpnI enzyme.

6. A recombinant DNA plasmid comprising a bacterial plasmid which contains a functional DpnII gene segment wherein said plasmid results in the production of DpnII enzyme following the transformation thereof into a bacterial strain suitable for production of DpnII enzyme.

* * * * *